United States Patent [19]

Clarke et al.

[11] Patent Number: 5,622,868
[45] Date of Patent: Apr. 22, 1997

[54] ANALYTICAL APPARATUS UTILIZING A COLORIMETRIC OR OTHER OPTICALLY DETECTABLE EFFECT

[75] Inventors: David J. Clarke, Salisbury; Freidoun Zamani-Farahani, Andover, both of United Kingdom

[73] Assignee: Microbiological Research Authority CAMR (Centre for Applied Microbiology & Research), Salisbury, United Kingdom

[21] Appl. No.: 465,192

[22] Filed: Jun. 5, 1995

Related U.S. Application Data

[63] Continuation of Ser. No. 209,380, Mar. 14, 1994, abandoned, which is a continuation of Ser. No. 778,872, filed as PCT/GB90/00658 Apr. 27, 1990 published as WO90/13017 Nov. 1, 1990, abandoned.

[30] Foreign Application Priority Data

Apr. 27, 1989 [GB] United Kingdom ............... 8909701

[51] Int. Cl.$^6$ .................................................. G01N 21/00
[52] U.S. Cl. ................... 436/147; 436/151; 436/164; 422/82.02; 422/82.09; 250/338.3; 356/432
[58] Field of Search .................. 422/56, 58, 82.01, 422/82.02, 82.05, 82.09, 82.12, 82, 86, 87, 90; 436/147, 149, 151, 152, 164, 169, 170, 177; 356/432, 432 T; 250/338.3

[56] References Cited

U.S. PATENT DOCUMENTS

| | | | |
|---|---|---|---|
| 3,772,518 | 11/1973 | Murayama et al. | 250/338.3 X |
| 3,861,879 | 1/1975 | Taylor | 422/98 X |
| 4,551,425 | 11/1985 | Zemel | 436/151 X |
| 4,557,603 | 12/1985 | Oehler et al. | 356/418 |
| 4,593,197 | 6/1986 | Miyatake et al. | 250/338.3 X |
| 4,654,127 | 3/1987 | Baker et al. | 422/82.01 X |
| 4,938,593 | 7/1990 | Morris et al. | 356/432 X |
| 5,108,576 | 4/1992 | Malmros et al. | 436/149 X |

FOREIGN PATENT DOCUMENTS

| | | |
|---|---|---|
| 0142481 | 5/1985 | European Pat. Off. |
| 3432972 | 3/1986 | Germany. |
| 0228066 | 9/1988 | Japan. |

OTHER PUBLICATIONS

Coufal et al. "Pyroelectric Calorimeter for Photothermal Studies of Thin Films and Adsorbates" Journal of Vacuum Science & Technology, vol. 5, No. 5, pp. 2875–2889 (1987).
Tanaka et al. "Pyroelectric Photothermal Spectroscopy for Thin Solid Films" Journal of Applied Physics, vol. 63, No. 6, pp. 1815–1819 (1988).

Primary Examiner—Jeffrey Snay
Attorney, Agent, or Firm—Browdy and Neimark

[57] ABSTRACT

Analytical apparatus includes a pyroelectric or other thermoelectric transducer element (10) in strip form. Thin film electrodes (12,14) are provided and one or more dots of reagent (16) are deposited on the transducer surface. A small amount of biological or other sample is deposited over the reagent dots which undergo selective colorimetric changes. The transducer is illuminated from below by LED light sources (24) and light absorption in the reagent regions is detected as microscopic heating at the transducer surface. The electrical signal output from the pyroelectric transducer is processed to derive analyte information.

26 Claims, 6 Drawing Sheets

ANALYTICAL APPARATUS UTILIZING A COLORIMETRIC OR OTHER OPTICALLY DETECTABLE EFFECT

This application is a continuation of parent application Ser. No. 08/209,380 filed Mar. 14, 1994, now abandoned, itself a continuation of grandparent application Ser. No. 07/778,872, filed as PCT/GB90/00658 Apr. 27, 1990 published as WO90/13017 Nov. 1, 1990, now abandoned.

FIELD OF THE INVENTION

This invention relates to analytical apparatus and methods of analysis, utilising the absorption at visible or other appropriate wavelengths of a reagent, analyte or related medium. The invention is particularly, though not exclusively, concerned with the biochemical assays

BACKGROUND OF THE INVENTION

A wide variety of current diagnostic and other biochemical tests employ a reagent which undergoes an eye detectable colour change in the presence of the analyte. The reagent is often conveniently carried on a test strip. Optics may be provided to assist the comparison of the observed colour change with a standard colour chart. Alternatively, the optical absorption may be measured at one or more selected wavelengths Whilst some arrangements permit the measurement of absorption through detection of transmitted light, reflectrometric arrangements are usually more convenient.

In many fields, the amount of sample available for analysis is very much restricted. It is accordingly desirable to have apparatus which is capable of analysing small drops or thin layers of sample. In many cases, immunoassay techniques being good examples, the thin layer approach has important further advantages. It becomes possible, for example, to immobilise the reagent (whether antibody or antigen) upon a surface and thus remove the need for a separation step. Examples of related techniques are enzyme-linked colorimetric assays and tests for other biochemical analytes.

In the particular field of immunoassays, the technique of internal reflection spectroscopy is known. A thin layer of sample material is established on a surface of a transparent optical element and measurements made of internal reflection of light at the interface with the sample. The same technique can be employed to measure fluorescence within the thin layer sample and other techniques have been suggested for detecting a shift in refractive index or polarisation.

A drawback of the techniques proposed hitherto is that they rely upon optical detection of reflected or transmitted light with subsequent signal processing providing the required measure of absorption, fluorescence or other optical parameter of interest. This is believed to have hindered the development of apparatus to meet the demands of specific applications. Thus, it is desirable in many applications to produce apparatus which is both compact and rugged. Under certain circumstances, where for example the analyte is potentially toxic or poses a microbiological contamination or health risk, it is desirable to have analytical apparatus of a form which is disposable after each analysis. In some cases, it would be advantageous to permit a number of analytical procedures to be conducted upon the same body of sample. The techniques employed hitherto do not lend themselves to embodiment in these forms.

SUMMARY OF THE INVENTION

It is an object of one aspect of this invention to provide improved analytical apparatus in which the need for optical detection systems is avoided.

It is a further object of one aspect of this invention to provide improved analytical apparatus which can take a simple and inexpensive form whilst retaining accuracy and reliability.

It is a still further object of one aspect of this invention to provide improved analytical apparatus in which dependence of results upon sample volume is diminished.

It is a further object of certain forms of this invention to provide analytical apparatus of sufficient sensitivity to enable multiple analytical procedures on one sample.

In one aspect, the present invention consists in analytical apparatus utilising a colorimetric or other optically detectable effect to provide an indication of analyte in a sample, the apparatus comprising transducer means having a transducer surface and adapted to provide an output signal indicative of energy absorption proximal said surface; means for establishing a body of sample at said surface; means for irradiating the sample at a frequency appropriate to detect said optical effect and processor means for receiving said transducer output signal and adapted to derive information therefrom regarding the analyte.

Advantageously, there is provided at said transducer surface at least one body of reagent, said reagent undergoing a colorimetric or other optically detectable change in the presence of the analyte.

Preferably, the transducer means comprises a solid state transducer element having electrode means formed on an external surface thereof.

Since the reagent is provided on a transducer surface sensitive to heat generation, light absorption in the reagent can be detected through localised heat generation. In the preferred case where the amplitude of the light source is modulated, periodic or pulsed heat generation can be detected in a manner which is ideally phase locked with the modulation of the illuminating light source.

The present invention envisages the use of a wide variety of transducers. In one form, a pyroelectric element serves as the transducer and a surface of that element receives the reagent.

In an important form of the present invention, said means for irradiating serves to direct light or other radiation through the transducer, which is arranged to be substantially transparent at the appropriate wavelengths.

It is quite possible to produce pyroelectric elements, such as polyvinylidene fluoride film, which are optically transparent. Similarly, techniques are available for the production of thin film electrodes which have sufficiently low absorption for this purpose.

An important further advantage offered by certain forms of the present invention is the ability to operate with small sample volumes without the difficulty found in certain existing apparatus that the results of the assay or detection are dependent upon the sample volume. In the existing apparatus, the proportion of the sample becoming bound or otherwise trapped within the body of reagent, can be significant in terms of the overall sample volume. There will accordingly be a shift in effective concentration which is volume dependent. In accordance with the present invention, the reagent volume—or as appropriate the reagent/transducer volume—can be made sufficiently small that the dependence on overall sample volume becomes negligible.

In a further aspect, the present invention consists in a method of analysis of a sample utilising transducer means having a transducer surface and adapted to provide an output signal indicative of heat generation at said surface, comprising the steps of establishing a body of sample at said surface; irradiating with electromagnetic radiation and monitoring said transducer output signal to derive through determination of heat generation at said surface a measure of absorption in the sample proximate said surface.

Advantageously, there is provided reagent at said surface, the reagent being selected to undergo a change in absorption in the presence of analyte in the sample.

Preferably, the step of irradiating with electromagnetic radiation comprises illuminating through the transducer means in the visible or near visible spectrum.

Suitably, the transducer means comprises electrode means at which said output signal appears.

In one form of the invention, the method includes one or more sample preparation, manipulation or processing steps comprising the application of voltage or current to said electrode means.

This invention is regarded as having a number of important advantages. Removing the need for detection optics should result in a considerable simplification and cost reduction. In appropriate cases it will be feasible to provide disposal transducer/reagent elements. The ability to work with drops of sample will often simplify sample preparation techniques. The fact that, in certain forms of the invention, a colour change is detected through the transducer, should remove or considerably reduce background interference, for example from the sample. The depth of the interfacial layer that is probed may if necessary be controlled by varying the frequency and amplitude of the illumination.

BRIEF DESCRIPTION OF THE DRAWINGS

The invention will now be described by way of examples with reference to the accompanying drawings in which.

DESCRIPTION OF THE PREFERRED EMBODIMENT

Figure 1:
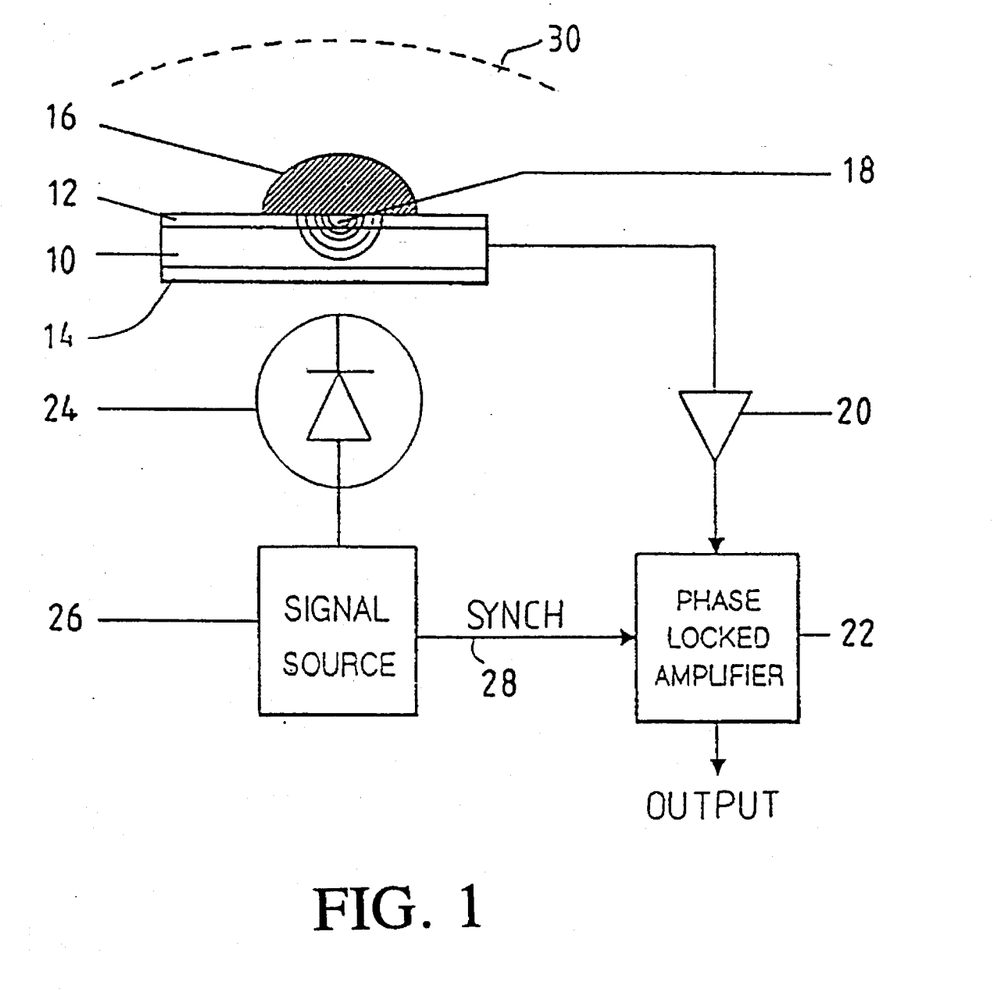
FIG. 1 is a schematic view of apparatus according to the present invention.

Referring initially to FIG. 1, a pyroelectric transducer comprises a PVDF film 10 having electrode coatings 12, 14 on the upper and lower surfaces respectively. The electrode coatings are in this example formed of sputter coated gold having a thickness in the range 5 to 15 nm. Strips of reagent 16 are deposited, using any suitable technique, upon the upper electrode coating 12. Each reagent strip may optionally carry on its upper surface a separation layer (not shown) to prevent interferents in the sample from coming into contact with the reagent. In many cases, however, such separation layers will be unnecessary.

The electrode coatings 12 and 14 are connected to the inputs of a charge amplifier 20 presenting a high input impedance, and the output of the charge amplifier is taken to a phase locked amplifier 22. A light source 24—taking in this example the form of a light emitting diode is positioned so as to illuminate the reagent strips through the pyroelectric film 10 and its associated electrode coatings. The light source is powered through a modulator 26 which provides a square wave output typically up to about 15 Hz. A reference signal is taken on line 28 from the modulator 26 to the phase locked amplifier 22.

In use, a drop of sample is deposited upon the upper surface of the pyroelectric transducer, the outline of the drop being shown in the drawing at 30. In the presence of levels of analyte, the appropriately chosen reagent undergoes a change in optical absorption. Light from the source 24 is absorbed in the reagent—the LED being of course selected to provide light of the appropriate frequency for the reagent in question—and the light absorption causes microscopic heating over a localised region shown generally at 8. This heating is sensed by the transducer and results in a change in output from the amplifier 20. Through phase locking on the reference signal on line 28, the amplifier 22 is able to provide a sensitive output signal indicative of the heating and thus of the light absorption within the reagent. The output of phase locked amplifier 22 can be handled in a variety of ways. It can be digitised and sent on an appropriate bus to a microcomputer. An alternative would be to filter the signal and take an analogue reading in a voltmeter.

The type of reagent chosen will vary widely depending upon the analytical procedure. For example, in tests for ions, pH and heavy metal indicator dyes may be employed which change colour on chelation/binding of ions. A variety of reagents are known for assays of metabolites, drugs and biochemicals in blood and urine. One example is a paracetamol assay with production of aminophenol from paracetamol by arylacylamidase. In immunological assays, the reagent may take the form of a protein or microbial antigen. The reagent may also be the antibody. The technique is also applicable to enzyme linked immuno-assays (ELISA).

The results achieved with the described apparatus can be illustrated with reference to FIG. 2 which is a calibration curve using a tetrazolium dye. This dye is commonly used for detecting oxidoreductase enzyme-linked reactions and is therefore suitable for use in a wide range of biochemical tests (ELISA) techniques. The dye acts as an electron transfer mediator for natural enzyme co-factors such as $NAD(P)^+$, (nicotine adenine dinucleotide (phosphate)).

Figure 2:
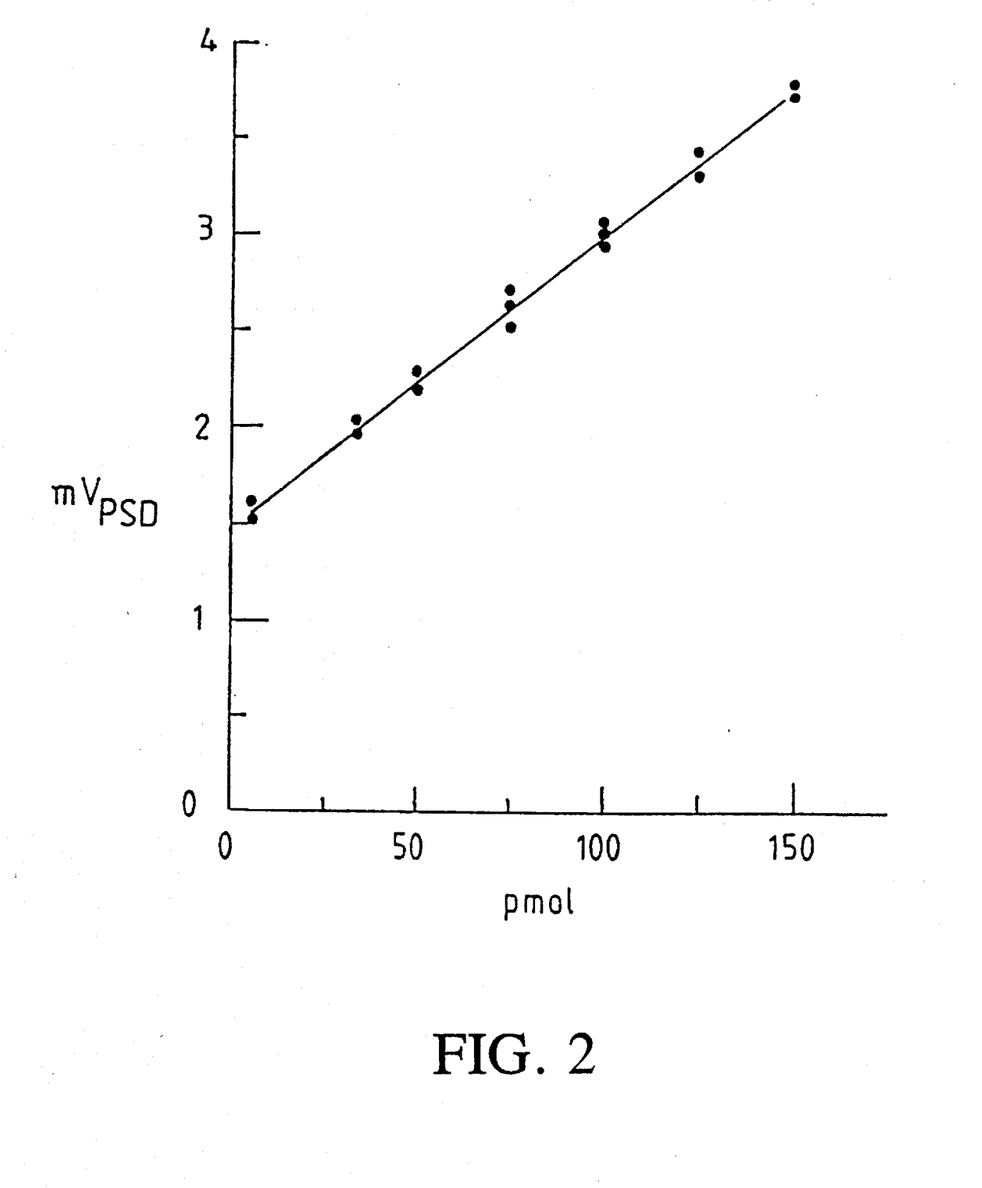
FIG. 2 is a graph illustrating the calibration of apparatus as shown in FIG. 1.

As will be seen from FIG. 2, there is a linear relationship between the voltage (expressed in mV) generated pyroelectrically across the electrodes 12,14 and the concentration of tetrazolium dye (expressed in picamoles).

It will be apparent that in use of the apparatus of FIG. 1, a particular frequency or frequency range will be selected which is appropriate for the reagent being used. The light source may be broad band, such as a flash lamp, or may be a light emitting diode, laser diode or other laser, selected as providing light at or around the appropriate wavelength. It may be necessary to select materials and thicknesses for the electrode coatings which are sufficiently transmissive at the selected frequency of operation. Other possible electrode materials are silver film, indium tin oxide or a nickel based alloy (as supplied on the commercially available Penwalt PVDF Film) etched if necessary to reduce the coating thickness. Coatings can be applied by ion beam, by sputtering or in other known ways. If it is inconvenient to provide an electrode coating which is sufficiently transmissive, appropriate windows may be created in both the electrode layers. Thus each reagent strip may be deposited directly upon the PVDF film with the electrode layer 12 then covering the film surface between the reagent strips. On the opposite surface, the electrode coating takes a similar form.

Illumination of the reagent/sample through the essentially transparent transducer formed by the PVDF film and thin film electrodes, has the important advantage of removing or considerably reducing the effects of spurious absorption or reflection in the sample. The apparatus is sensitive only to absorption at a narrow surface region overlying the transducer surface. The ability to operate with small sample volumes is of considerable importance, as will be well understood. Moreover, the present invention reduces the problem of sample volume dependence which has significantly reduced the usefulness of earlier suggested "small sample volume" techniques. Specifically, the reaction volume of apparatus according to this invention, that is to say the reagent/sample volume where optical absorption contributes to the detected heat change, is small compared even with the small sample volume.

The described apparatus also offers improved kinetic characteristics, particularly the avoidance of inhomogeneous colour changes arising—for instance—from incomplete mixing of reagent/sample. Established large surface area test strip devices require complex sample mixing and spreading procedures if reproducible results are to be achieved. In addition, problems can arise with these and other chemical and biosensor devices where the test involves significant analyte consumption. Examples of such tests are amperometric electrochemical sensors, enzyme-linked tests, enzyme electrodes and some affinity reactions. Unless there is thorough and continuous stirring, erroneous results can arise from depletion of analyte in the unstirred layer proximal to the device surface. The very small reaction volume utilised in the present invention avoids such difficulties.

This invention can readily provide for multiple tests on the same sample. By way of illustration, reference is now directed to FIGS. 3 and 4

Figure 3:
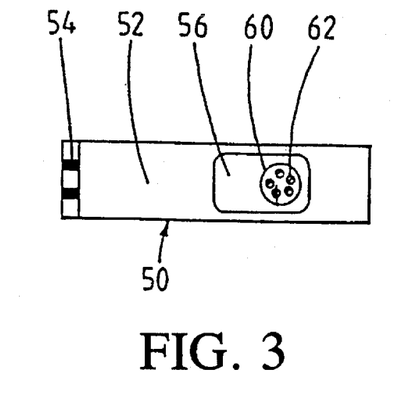
FIG. 3 is a plan view of a test element forming part of apparatus according to a further embodiment of the present invention.

In this example, a test element 50—which may be disposable—comprises an inept substrate 52 of rectangular form. At one end, the strip 52 is provided with electrical connections 54 enabling the test element to be plugged into test apparatus. The substrate 52 carries a pyroelectric strip 56 in the form of a PVDF film. This PVDF film can, as shown in FIG. 3, be deposited upon the substrate 52; alternatively, the PVDF film may be stretched across a window cut in the substrate.

Figure 4:
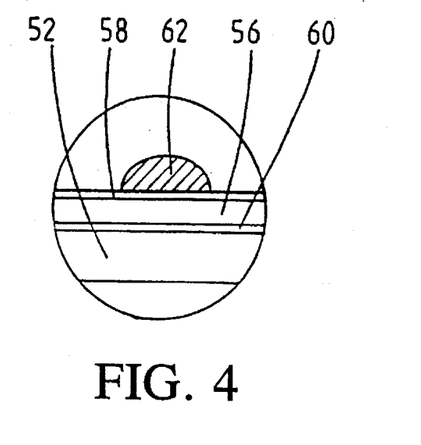
FIG. 4 is an exploded part sectional view of FIG. 3.

The pyroelectric strip 56 carries upper and lower thin film electrodes 58 and 60. On the upper surface, there is defined a sample loading spot 60 and, within this spot, five distinct reagent regions 62 are provided.

Figure 5:
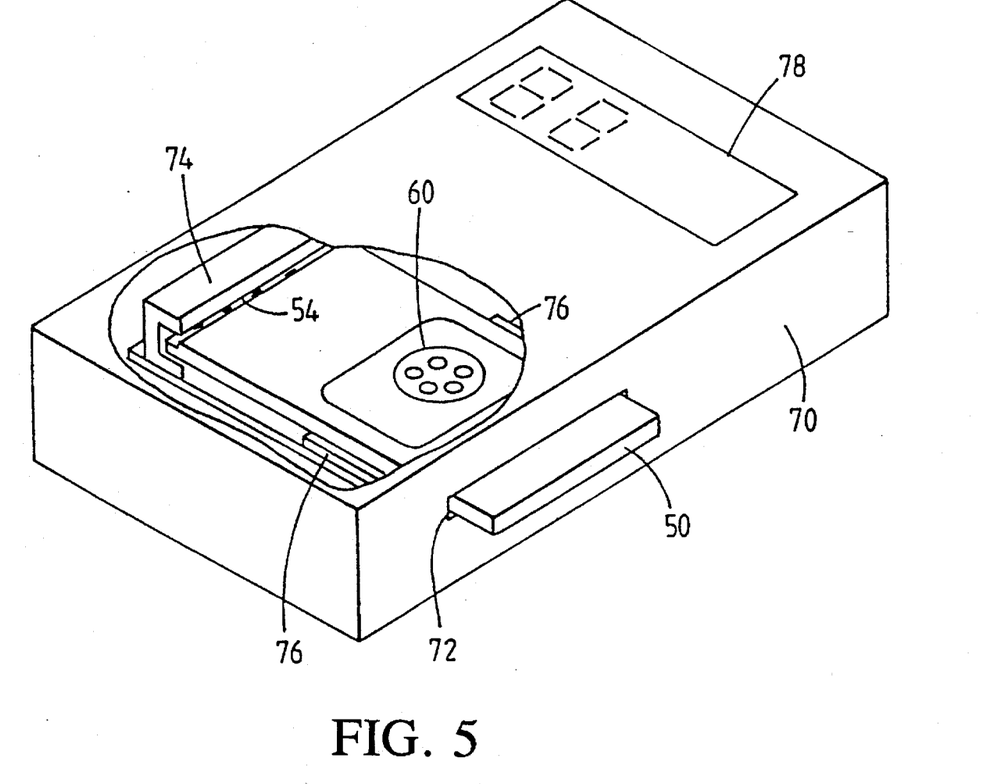
FIG. 5 is a perspective sketch of hand-held test apparatus for use with the test element of FIG. 3.

The test element 52 can be used with hand-held test apparatus as illustrated in FIG. 5. Referring to that Figure, a housing 70 is provided with a slot 72 into which the test element 50 can be slidingly engaged. Internally, the housing provides an edge connector 74 designed to mate with the electrical connectors 54 on the test element 50. An LED light source shown schematically at 76 is positioned within the housing 70 so as to be aligned with the sample spot 60 when the test element 50 is fully engaged.

The test apparatus contains battery powered circuitry (not shown) providing the modulated signal source, charge amplifier and phase locked amplifier as described with reference to FIG. 1. There is further provided a microprocessor, which may be of commercially available form, which is connected to receive the output of the phase locked amplifier and to control—through an appropriate device driver—a display 78.

The test element 50 can, if appropriate, be of disposable form, this removes problems of contamination and of cleaning possibly hazardous sample material. The arrangement by which a preprepared test element, after contacting with a drop of sample, is simply pushed into test apparatus takes advantage of the simplicity inherent in this invention and offers considerable practical advantages without sacrificing experimental accuracy.

The different reagent regions 62 can, as will be described in more detail later, be illuminated sequentially using essentially a common transducer or simultaneously with the electrode films and PVDF film then fashioned so as to provide effectively separate transducers for the respective reagent regions.

The ability to conduct multiple tests on the same sample is useful in a number of ways. Clearly, the use of different reagents will enable two or more different assays to be conducted simultaneously. This is particularly useful where the amounts of available sample are limited. It is also possible to arrange for automatic compensation through comparison between different reagent strips. This technique can be employed to compensate for any device to device or batch to batch variation in manufacture or to compensate for an interfering physical change (for example thermal, acoustic or optical) it will also be possible to provide for "in-built" reagent calibration by including internal standards of analyte in a reagent layer to compensate for any biochemical interference effect or for variability in reagents.

The invention will also have applications in the field of electrophoresis. At present, a sample in gel form is sandwiched between glass plates or mounted upon a suitable substrate and, after electrophoresis has taken place, stained with appropriate dyes. The separated components can then be identified visually or analysis can be conducted automatically using a scanning optical densitometer. According to the present invention, the gel is mounted directly upon the PVDF film and after electrophoresis has taken place, absorption is determined in a manner analogous to that described above.

Figure 6:
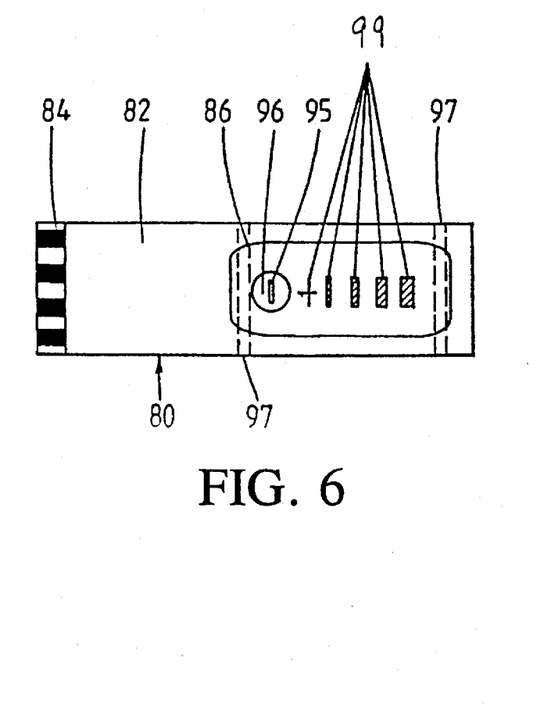
FIG. 6 is a view similar to FIG. 3 showing a further embodiment of the present invention.
Figure 7:
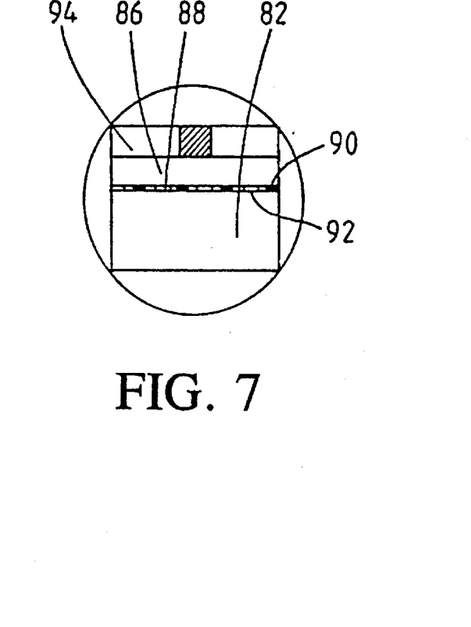
FIG. 7 is an exploded part sectional view of FIG. 6.

Referring now to FIGS. 6 and 7, there is shown a test strip 80 adapted for use in electrophoretic analysis. The test element 80 has, in common with that of FIG. 3, a substrate 82 with electrical connections 84. The substrate carries an elongate pyroelectric strip 86 provided (in contrast with the previous arrangement) with an electrode layer 88 on the underside only. This electrode layer comprises two interleaved electrode structures with alternate parallel electrode strips such as 90 and 92 "belonging" to different electrode structures. In this way, an electric field created in the pyroelectric film, over a region comparable in dimension with the inter-electrode spacing, can be detected as a potential difference across the respective electrode structures.

The pyroelectric film 86 carries on its upper surface a layer of electrophoretic separation gel 94. A well 95 cut into the gel at a sample loading spot 96. At opposite ends, field electrodes 97 are provided within the gel which lie parallel with the electrode strips 90, 92. The electrodes 97 are connected through further leads with the electrical connections 84.

In use, sample deposited at the sample loading spot 96 will, through well 95, be loaded into the electrophoretic gel and under the action of an electric field applied across electrodes 97, species within the sample will travel along the strip to form separated bands, as illustrated at 99. Subsequently, the test element can be loaded into test apparatus as described above for determination of the band positions through light absorption. A typical example of this technique is the rapid detection of glycosylated haemoglobin. This test is known as a useful means of determining whether diabetics are controlling their glucose levels effectively, because protein glycosylation reflects the level of glucose in the blood over a period of weeks or months depending principally upon the half life of the protein in blood. Glucose test of course only provide a measure of instantaneous glucose levels. In this application, the natural red colour of haemoglobin is detectable without staining. Glycosylated fractions can be electrophoretically separated by a number of established techniques, for example invoking electroendosmosis in agar medium or differential affinity of the glycosylated form using sugar binding lectins or antibodies bound to the separation medium.

Identification of the position of the separated bands using the detection of localised heat generation on light absorption in the bands, provides a very simple method for detecting glycosylated haemoglobin, and a wide variety of other electrophoretic analyses. These may involve naturally coloured o stained analytes and any convenient separation medium. If appropriate, the electrophoretic separation can be conducted contemporaneously with determination of band position. That is to say, the hand-held or other test apparatus can include the higher voltage supply required for the electrophoresis field electrodes, together with the appropriate timing controls.

Detecting the position of electrophoretically separated bands requires, as with the multi-analyte test described with reference to FIG. 3, a degree of spatial resolution. Examples of techniques by which such spatial resolution can be provided will now be described with reference to FIGS. 8, 9, 10, 11, 12, and 13.

Figure 8:
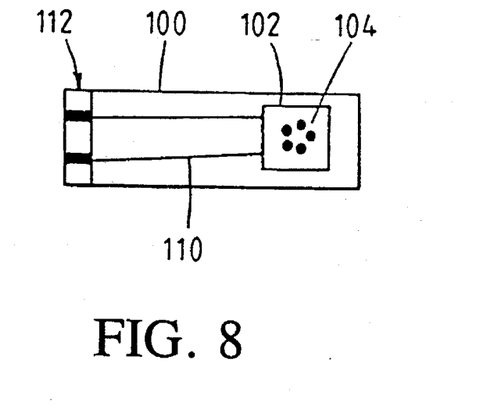
FIG. 8 is a plan view of a test element forming part of apparatus according to a still further embodiment of the present invention.
Figure 9:
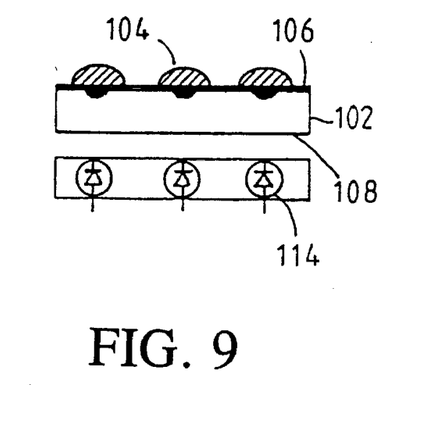
FIG. 9 shows a section through the test element of FIG. 8) together a schematic representation of the corresponding light source.

Referring initially to FIG. 8, there is shown schematically a test strip 100 having a pyroelectric region 102 provided with five separate reagent regions such as 104. As shown in FIG. 9, the pyroelectric layer 102 has continuous electrode layers 106, 108 on its upper and lower surfaces respectively. These two electrode layers are connected through leads 110 with an electrical connector 112 comprising a simple pair of contacts.

In this embodiment, there is essentially a common transducer element serving the five reagent regions. To enable separate determinations to be made of different analytes, the light source comprises an array of five separate LED's 114 which are aligned respectively with the reagent regions and energised sequentially. If necessary, an appropriate mask can be introduced between the test element and the diode array so as to eliminate cross-talk.

It would be recognised that in this way, the common transducer represented by the pyroelectric film and its associated electrodes, is effectively multiplexed between the reagents responsive to the different analytes. The sequential illumination of different regions of the test element can of course be achieved in a variety of ways beyond the described diode array. One alternative, for example, would employ a single light source optically switched between five optical fibres each terminating adjacent the corresponding reagent.

Figure 10:
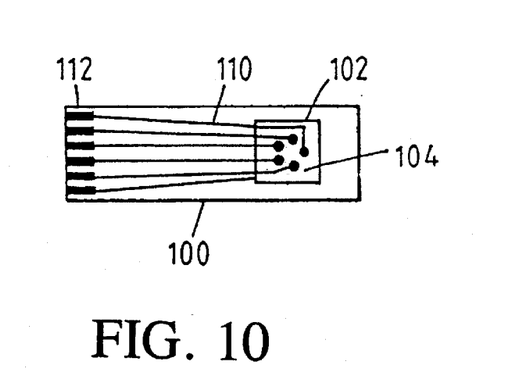
FIGS. 10, 11, 12, and 13 are similar to FIGS. 6a) & b) but illustrating modifications.
Figure 11:
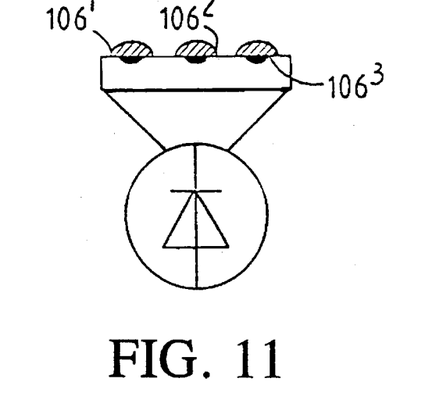

Referring now to FIGS. 10 and 11, there is shown a modification in which the upper electrode is divided into distinct electrode regions such as 106$^1$, 106$^2$ and 106$^3$ which underly the respective reagent regions 104 and ape connected through individual leads 110 to the electrical connector 112. In this case the connector comprises six contacts connected respectively with the five upper electrode regions and the lower electrode layer 108. With this arrangement, a single diode 114 can be employed to illuminate all five reagent regions simultaneously. The sub-division of the upper electrode layer provides five effectively separate transducers each detecting heat generated on absorption within the corresponding reagent.

Figure 12:
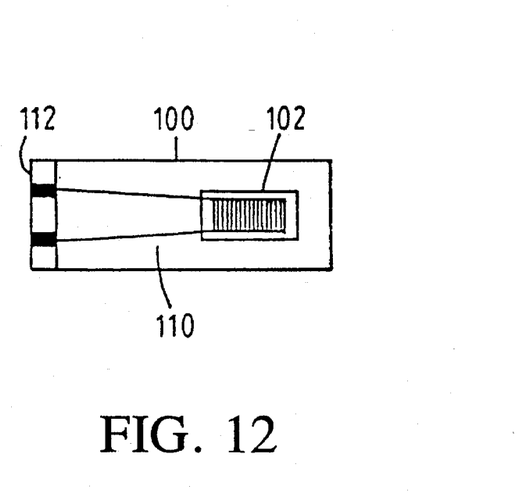
Figure 13:
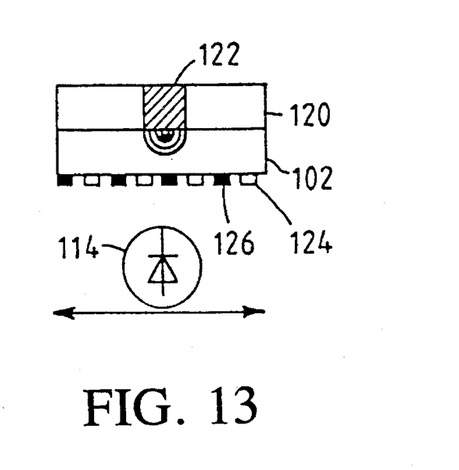

A still further alternative will be described with reference to FIGS. 12 and 13 which show a test strip 100 adapted for electrophoretic separation. The pyroelectric layer carries (as with the FIGS. 5 and 6, a layer of electrophoresis separation gel 120 enabling the electrophoretic separation of bands such as that shown at 122. The underside of the pyroelectric layer 102 carries two interleaved electrode structures which are connected through leads 110 with an electrical connector 112 comprising a simple pair of contacts. As with the FIGS. 5 and 6 embodiment alternating parallel electrode strips such as 124 and 126 are connected with opposite electrode structures. Means (not shown) are provided for generating the electrophesis electrical field.

To provide the necessary spatial resolution, a scanning light source is provided in the form of a light emitting diode 114 which is capable of movement along the length of the strip 100. The variation with time of the output signal from the effectively common transducer thus providing a measure of the optical density variation through the band structure.

It will be recognised that the scanning light source can be provided in a variety of other ways; one example employs a fixed laser diode producing a beam which is scanned across the band structure.

It should be recognised that the arrangements of FIGS. 8 to 13 have been chosen as examples only. It would be possible, for example, to employ in the electrophoretic test element of FIGS. 12 and 13 the spatial diode array of FIGS. 8 and 9. In that case, however, a linear rather than an arial array would suffice. Also, it will be possible to use in the arrangements of FIGS. 8 to 11 (and indeed in other forms of this invention) the interleaved electrode structure of FIGS. 12 and 13. The advantage of having electrodes on one side only of the pyroelectric film is—in electrophoresis—that an electrode adjacent the separation gel would tend to short circuit the applied separation electric field. There is, however, the more general advantage of having no electrode on the upper surface of the pyroelectric film, this being of reducing the thermal conductivity which would otherwise tend to dissipate heat generated and reduce the spatial definition of the device.

In a more sophisticated arrangement, a spatial electrode array can be designed to permit a Fourier or Hadamard transformation to improve resolution.

Figure 14:
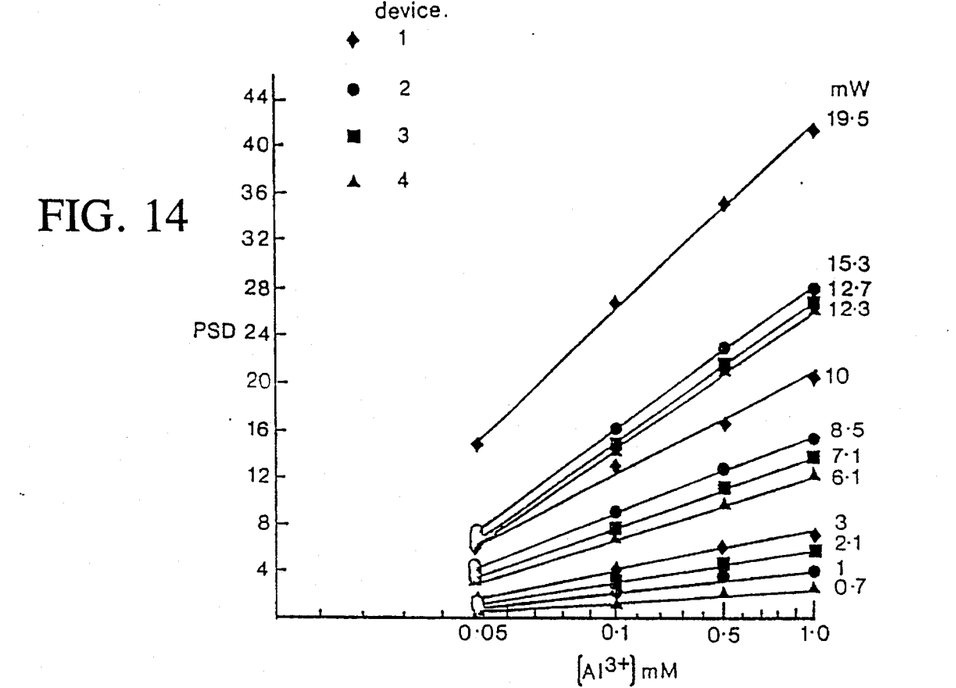
FIG. 14 is a graph illustrating experimental evaluation of apparatus generally as shown in FIG. 1.

The method and apparatus according to this invention has been evaluated experimentally using various concentrations of aluminium ions with four separate devices at varying incident light power levels. There is shown in FIG. 14 a plot of transducer output in millivolts against a millimolar concentration of aluminium ions. As shown, measurements were taken at various incident light power levels and with separate devices numbered 1 to 4. It will be seen that, for each device and incident light power level, there is a linear relationship between concentration and transducer output.

Figure 15:
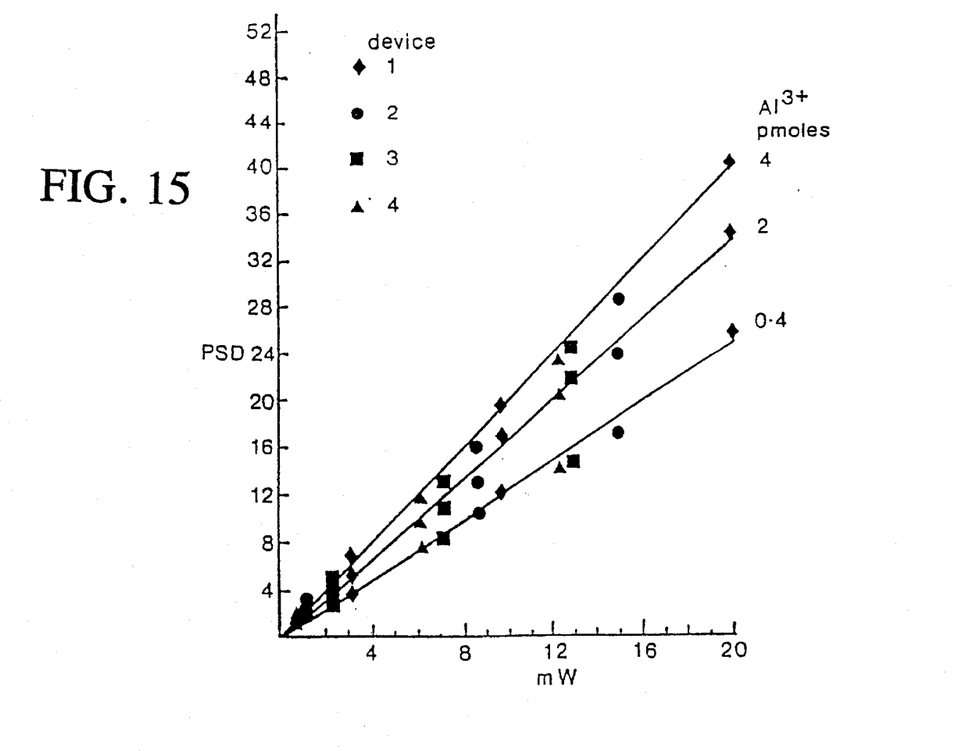
FIG. 15 is a graph depicting the data of FIG. 14 after further processing.

By calculation from the data of FIG. 14, a measure can be obtained, of the quantity in moles of aluminium detected. Replotting of the calculated data in FIG. 15 shows that for a particular concentration of aluminium ions and thus a particular absorption coefficient, there is a linear relationship between incident light power and measured transducer output.

Figure 16:
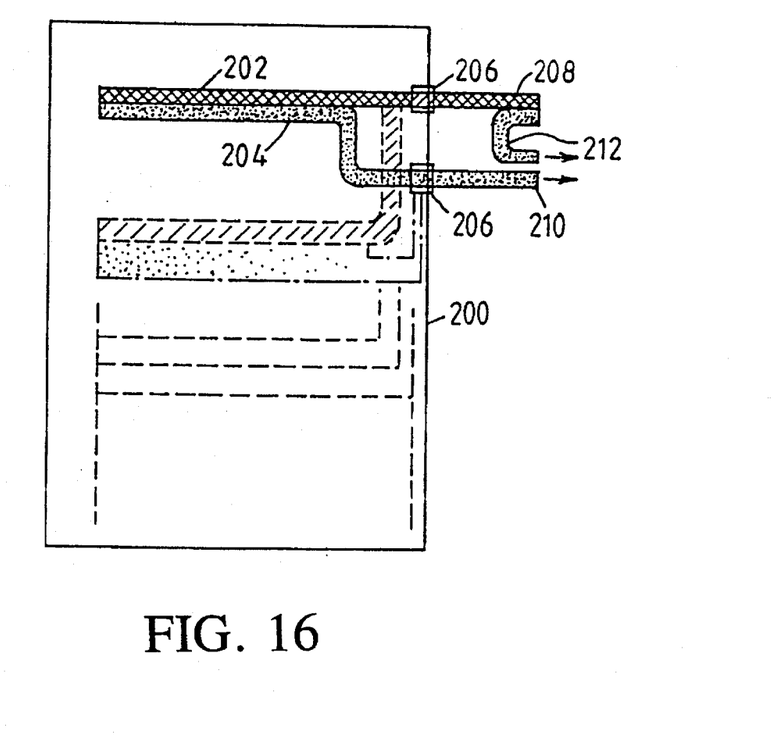
FIG. 16 is a sketch illustrating yet a further modification.

Whilst the example has been taken in the above embodiments of a pyroelectric transducer and particularly PVDF film, it will be understood that there are a great variety of other transducers capable of detecting heat generation at a surface. A thermoelectric transducer may, for example, be employed transducing the heat pulse using the electromotive force arising between two dissimilar metals or a metal and a semiconductor at different temperatures (thermocouple or Seebeck effect). Referring to FIG. 16, there is illustrated schematically a transducer including a thermocouple. The transducer is in sheet form with an appropriate polymeric substrate 200. Parallel strips of platinum 202 and platinum/rhodium 204 are arranged in pairs with the strips of each pair lying in electrical contact along most of their length. Towards their right hand ends, the strips 202, 204 of each pair separate to form electrical contacts 206. External connections 208 and 210 are of platinum and platinum/rhodium respectively to avoid introducing further dissimilar metal junctions. At connection 208, a reference junction is formed with bridge piece 212 of platinum/rhodium. Connections are taken from bridge piece 212 and connection 210 to a voltmeter (not shown). It will be recognized that with the reference junction maintained essentially at constant temperature, temperature variations at the junction between strips 202 and 204 are detectable as voltage changes. The remaining pairs of strips can either be connected in parallel within the transducer, as shown in FIG 16, or provided with individual external connections and reference junctions. The latter alternative will, as understood, provide spatial resolution of heat generation over the transducer surface.

The strips of platinum and platinum/rhodium may be deposited sufficiently thinly to transmit light.

In a further alternative (not illustrated), a thermoresistive transducer may be employed which serves to transduce the heat pulse in terms of the change in resistance of a metal or semiconductor. There are a wide variety of materials suitable for use in this fashion, one example of which is ruthenium oxide, which when provided with thin film electrodes, can be made sufficiently light transmissive. Still other transducers may be employed which operate upon the temperature dependent behaviour of a photoelectric device. A Further alternative is to utilise a heat-dependent shift in refractive index as detected in a simple detector measuring, for example, reflection at a boundary between the material of variable refraction index and a material having a small thermal coefficient of refractive index.

The invention further envisages detection of energy absorption proximal the transducer surface by virtue of the mechanical energy arising on localised thermal expansion. A piezoelectric transducer may accordingly be employed to detect mechanical deformation. A thermocapacitive transducer may operate from the change in capacitance arising from mechanical deformation of a small plate capacitor. It should also be mentioned here that a thermocapacitive transducer can be utilised to sense a temperature dependent change in permittivity of a dielectric material. The mechanical energy may further be sensed through a magnetostrictive effect or through a optical-mechanical effect such as the production of free radicals on conversion of intense localised mechanical energy.

The electrical circuitry required to process the transducer output signal will of course depend upon the nature of the transducer. A form of phase sensitive detector locked to the modulation of the light or other radiation source will usually be preferred.

In particular forms of the method according to this invention, advantage can be taken of the electrode structure used for taking the output signal from the transducer means in order to apply voltage or current to the sample reagent. Thus, in one example, electrophoresis could be performed with an electric field applied through the same electrodes as used subsequently for generating the transducer output. The electrode means could also be used to electro-elute separated fractions off the electrophoresis gel and, with appropriate electrode patterns, could be used to electro-elute particular bands identified by photothermal detection within an automated instrumentation system.

Further examples of the use of electrode means in sample preparation, manipulation or processing steps include the application or detection of electrochemical potentials in spectroelectrochemical assays; releasing intracellular analytes by the application of high voltages to permeate cells; increasing the rate of interaction of macro-molecules using low amplitude alternating electrical signals and promoting aggregation of macro-molecules (for example antibody/antigen) using appropriate electrical fields.

In the case where the transducer element exhibits a piezoelectric effect, as for example does polyvinylidene fluoride, voltages can be applied to the electrode means to perform mechanical work on the sample. Thus, for example, the rate of reaction can in appropriate cases be increased by ultrasonic irradiation of the sample and reagent, sample or reagent particles can be manipulated in higher frequency acoustic fields to separate interference or to concentrate inter-acting particles, or to disrupt cells or other particles using cavitating fields and surface shear effects.

It should be understood that whilst the invention has been described largely in terms of colorimetric analyses it is not restricted in this regard. It is also applicable to measurements of changes in effective absorption where, for instance, the analyte has an effect on light scattering in the reagent. An example here is immunoaggregation of erythrocytes. Alternatively, re-absorption of fluorescence within a sample can be detected. The wavelength need not be in the visible spectrum and the term "optically detectable" as used herein should not be regarded as restrictive in that sense. Measurements can be made example in the UV range. It should also be noted that the change need not be confined to the reagent; a colorimetric change may be detected in the analyte or in the medium. Indeed, the present invention will find application in measuring the absorption of a sample layer without the presence of a reagent. One example is of course the determination of band position on electrophoretic separation of a stained or naturally coloured analyte, but still further examples exist, such as optical density measurements of naturally coloured biological and other samples.

We claim:

1. A method of analysis of a sample, utilising transducer means having a transducer surface, there being provided at said transducer surface at least one electrophoretic separation layer and a colorimetric reagent thereon; comprising the steps of establishing a body of sample at said surface; effecting separation of species within the sample in the place of the separation layers; irradiating said sample with electromagnetic radiation such that heat is generated by the absorption of said electromagnetic radiation; and monitoring said transducer output signal to derive through determination of said heat generation at said surface, a measure of absorption in the sample proximate the surface.

2. A method according to claim 1, comprising the further step, prior to said irradiation step, of applying an electric field to said sample.

3. A method according to claim 1, comprising the further step, contemporaneously with said irradiating step, of applying an electric field to said sample.

4. Analytical apparatus utilising a colorimetric effect to provide an indication of analyte in a sample, said colorimetric effect representing a change in absorption at a known frequency of light, the apparatus comprising:
   a pyroelectric transducer having electrode means and a transducer surface, a voltage signal at said electrode means being indicative of heat generated proximal said transducer surface;
   a body of reagent provided at said transducer surface;
   means for irradiating with visible light at said frequency, a body of sample provided at said transducer surface, whereby heat is generated in an amount representative of said absorption; and
   processor means for receiving said voltage signal and constructed so as to derive said indication of the analyte.

5. Apparatus according to claim 4, wherein there is provided spaced over at said transducer surface a plurality of distinct bodies of reagent, at least some of said reagent bodies being responsive to different analytes in the sample.

6. Apparatus according to claim 4, wherein said pyroelectric transducer is substantially transparent at said known frequency of light and said means for irradiating is constructed so as to irradiate said body of sample through the pyroelectric transducer.

7. Biochemical analytical apparatus utilising a colorimetric effect to provide an indication of one or more analytes in a sample, said pyroelectric effect representing a change in absorption at a known frequency of light, the apparatus comprising a solid state transducer means having electrode means and a transducer surface and constructed so as to provide an output signal at said electrode means indicative of heat generated proximal said transducer surface, the cross-sectional structure of said transducer means perpendicular to said transducer surface being uniform over said surface; a plurality of distinct bodies of reagent provided at said transducer surface; means for establishing a body of sample at said surface in contact with said bodies of reagent; means for irradiating the sample with light at said known frequency, whereby heat is generated in an amount representative of said absorption and processor means for receiving said transducer output signal and constructed so as to derive said indication of the analyte or analytes.

8. Apparatus according to claim 7, wherein said transducer means comprises a pyroelectric element.

9. Apparatus according to claim 7, wherein there is provided at said transducer surface, in operative association with one of said reagent bodies, a known concentration of a substrate to which one of said reagent bodies is responsive thereby to provide calibration information.

10. Apparatus according to claim 7, wherein said transducer means comprises a plurality of transducer elements associated respectively with said reagent bodies.

11. Apparatus according to claim 7, wherein said means for irradiating comprises means for irradiating said reagent bodies sequentially.

12. Apparatus according to claim 7, wherein said means for irradiating comprises an amplitude modulated source with said processor means receiving a reference signal indicative of the phase of modulation of said source.

13. Apparatus according to claim 7, wherein said solid state transducer means is substantially transparent to light at said known frequency.

14. A method of biochemical analysis through measurement of the absorption of a sample at a known frequency of light, utilising a pyroelectric transducer means having a transducer surface and a colorimetric reagent thereon and constructed so as to provide an output signal indicative of heat generation at said surface; comprising the steps of establishing a body of sample at said surface; irradiating said sample with light of said known frequency such that heat is generated through said absorption; and monitoring said transducer output signal to derive said biochemical analysis through determination of said heat generation.

15. A method according to claim 14, wherein said irradiating step is conducted with a modulated source and said monitoring step is carried out with phase locking to said modulation.

16. A method according to claim 14, further comprising the step of providing at said transducer surface an electrophoretic or similar separation layer and, subsequent to the establishment of a body of sample at said surface, the step of effecting separation of species within the sample in the plane of the separation layer.

17. A method according to claim 16, comprising the further step, prior to said irradiating step, of applying an electric field to said sample.

18. A method according to claim 16, comprising the further steps contemporaneously with said irradiating step, of applying an electric field to said sample.

19. A method according to claim 14, further comprising the step of providing at said surface at least one body of reagent selected to undergo a change in absorption in the presence of analyte in the sample.

20. A method according to claim 19, wherein said monitoring step comprises providing spatial resolution of heat generation over said surface.

21. A method according to claim 20, wherein said irradiating step comprises the sequential irradiation of different regions of said surface.

22. A method according to claim 20, wherein said transducer means comprises a plurality of transducers having said transducer surface in common.

23. A method of biochemical analysis of a sample utilising a colorimetric effect to provide an indication of analyte in a sample, said colorimetric effect representing a change in absorption at a known frequency of light, the method utilising a solid state transducer mean substantially transparent at said known frequency and having a transducer surface with a plurality of distinct bodies of reagent provided thereon and constructed so as to provide an output signal indicative of heat generation at said surface; comprising the steps of establishing a body of sample at said surface in contact with said bodies of reagent; irradiating said sample through the transparent transducer means with light of said known frequency such that heat is generated by light absorption and monitoring an output signal from said transducer means to derive information regarding the sample through spatially resolved determination of heat generation at said surface.

24. A method according to claim 23, wherein said irradiating step comprises the sequential irradiation of different regions of said surface.

25. A method according to claim 23, wherein said transducer means comprises a plurality of transducers having said transducer surface in common.

26. Biochemical analytical apparatus utilising a colorimetric effect to provide an indication of analyte in a sample, said colorimetric effect representing a change in absorption at a known frequency of light, the apparatus comprising:

a pyroelectric transducer having electrode means and a transducer surface, a voltage signal at said electrode means being indicative of heat generated proximal said transducer surface, the pyroelectric transducer being substantially transparent at said known frequency of light;

a plurality of distinct bodies of reagent provided at said transducer surface;

mans for irradiating with visible light at said frequency, through the pyroelectric transducer, a body of sample provided at said transducer surface, whereby heat is generated in an amount representative of said absorption; and processors means for receiving said voltage signal and constructed so as to derive said indication of the analyte.

* * * * *